United States Patent [19]
Green

[11] 4,456,687
[45] Jun. 26, 1984

[54] AGENTS FOR PROMOTING GROWTH OF EPITHELIAL CELLS

[75] Inventor: Howard Green, Brookline, Mass.

[73] Assignee: President and Fellows of Harvard College, Cambridge, Mass.

[21] Appl. No.: 211,921

[22] Filed: Dec. 1, 1980

Related U.S. Application Data

[63] Continuation of Ser. No. 961,444, Nov. 16, 1978, abandoned.

[51] Int. Cl.$^3$ .............................................. C12N 5/02
[52] U.S. Cl. ...................................... 435/241; 435/2; 435/240
[58] Field of Search .......................... 435/2, 240, 241

[56] References Cited

PUBLICATIONS

Chopra–Chem. Abst., vol. 86 (1977), p. 183,032e.
Hollenberg et al.–Proc. Nat. Acad. Sci., vol. 70, No. 10, (1973), pp. 2964–2968.
Rieber et al.–Cancer Research, vol. 35, No. 11, pt. 1 (Nov. 1975), pp. 3009–30013.
Hollenberg et al.–Proc. Nat. Acad. Sci., vol. 71, No. 10 (Oct. 1974), pp. 4224–4228.

Primary Examiner—Sam Rosen
Attorney, Agent, or Firm—Arthur A. Smith, Jr.; David E. Brook

[57] ABSTRACT

Certain agents are disclosed which promote growth of epithelial cells, including human epidermal cells. These agents are known to increase the level of cellular cyclic-AMP.

13 Claims, No Drawings

AGENTS FOR PROMOTING GROWTH OF EPITHELIAL CELLS

GOVERNMENT SPONSORSHIP

The invention described herein was made in the course of or under grants from the National Institutes of Health.

This is a continuation of application Ser. No. 961,444, filed Nov. 16, 1978, abandoned.

BACKGROUND OF THE INVENTION

1. Field of the Invention

This invention is in the field of biology and more particularly relates to the field of cell biology.

2. Description of the Prior Art

Epithelial cells are cells covering or lining body surfaces. Examples include epidermal cells of the skin and cells lining the mouth, nose, pharynx, esophagus and vagina. Many epithelial cells, though not all, are often referred to as keratinocytes because of their ability to synthesize keratin.

Although techniques for cultivation of many types of mammalian cells have long been known, most efforts to serially cultivate normal epithelial cells, including mammalian epidermal cells, have failed. Some of the numerous literature descriptions of attempts to serially cultivate disaggregated epidermal cells in monolayers are included in: F. L. Vaughan and I. A. Bernstein, *J. Invest. Derm.*, 56, 454 (1971); M. A. Karasek and M. E. Charlton, *J. Invest. Derm.*, 56, 205 (1971); N. E. Fusenig and P. K. M. Worst, *J. Invest. Derm.*, 63, 187 (1974); and S. H. Yuspa, D. L. Morgan, R. J. Walker and R. R. Bates, *J. Invest. Derm.*, 55, 379 (1970).

More recently, a technique was discovered for the serial cultivation of epidermal cells (keratinocytes) under very specific and controlled conditions. In this technique, human epidermal cells were grown in cultures together with fibroblast cells treated to prevent their multiplication. Fibroblast cell density was carefully controlled to allow epidermal cell colony formation and growth. It was also disclosed that some keratinocytes could be grown when fibroblast cell products were substituted for the fibroblast cells themselves. These techniques for serially cultivating epidermal cells and other epithelial cell types are described in U.S. Pat. No. 4,016,036 issued to Howard Green and James G. Rheinwald.

DESCRIPTION OF THE INVENTION

This invention relates to the surprising discovery that agents known to increase the level of cellular cyclic-AMP can provide a dramatic effect on the growth of epithelial cells. Thus, such agents can be employed in the serial cultivation of epithelial cells employing the techniques disclosed by Green et al. in U.S. Pat. No. 4,016,036, or in other growth techniques for epithelial cells.

Four agents have been tested and found to increase multiplication of human epidermal cells. These agents are cholera toxin, dibutyryl cyclic-AMP, methyl isobutyl xanthine and isoproterenol. These agents are known to increase the cell content of cyclic-AMP in epidermal cells, as well as other cell types.

The only known common property of the four agents actually found to increase proliferation of epidermal cells is their ability to increase cellular levels of cyclic-AMP. In addition, their is no well established case of a vertebrate tissue whose adenyl cyclase activity cannot be made to rise by cholera toxin and no effects of the toxin on cell behavior other than those mediated by cyclic-AMP are known.

The different agents produced effects of differing magnitude. Cholera toxin produced the strongest effects. The effects produced by dibutyryl cyclic-AMP were definite but much smaller. The effects of isoproterenol and methyl isobutyl xanthine were considerably larger than the effects of dibutyryl cyclic-AMP, but still smaller than those of cholera toxin.

Although each of these agents is known to increase the cellular level of cyclic-AMP, they do not do so by a single mechanism. Cholera toxin and isoproterenol are known to increase cellular cyclic-AMP by activation of adenyl cyclase. Methyl isobutyl xanthine increases cyclic-AMP by inhibiting phosphodiesterase, the enzyme which hydrolyzes cyclic-AMP. Dibutyryl cyclic-AMP acts either by inhibiting phosphodiesterase or by imitating the actions of cyclic-AMP, of which it is an analog.

The appropriate concentration of agent will depend upon certain factors, including which agent is employed, which epithelial cells it is desired to stimulate, whether the growth is in culture or in vivo, and other such factors. It is very likely that the dosages will be different in each case. As an example, it has been found that human epidermal cells grown in culture in the presence of lethally irradiated 3T3 mouse fibroblast cells can be stimulated with cholera toxin at concentrations as low as $10^{-13}$ molar. On the other hand, much higher concentrations of cholera toxin are likely to be more efficacious and can be employed since cholera toxin has a low level of toxicity except for the intestines. Information regarding dosages for each of these agents employed with a specific set of conditions is given in the Examples presented below. This information, coupled with other known data, e.g., toxicities, will be helpful to those skilled in the art in choosing or determining appropriate dosages for a given application.

Although most experiments described herein were carried out with epidermal cell cultures optimally supported by irradiated 3T3 mouse fibroblast cells, as described in U.S. Pat. No. 4,016,036, it was observed that when the 3T3 cells were usually sparse or unhealthy, the effect of cholera toxin was, if anything, more striking, so that cultures which otherwise had to be discarded were able to grow quite well.

Additionally, epidermal growth factor was employed in many of the experiments carried out, although it is not required. Although epidermal growth factor displays some effects in common with those of cholera toxin, there are important differences indicating that epidermal growth factor has a different mechanism of action. Cholera toxin increased the numaber of cells in growing colonies at the earliest time that they could be observed; microscopic examination gave the impression that colonies contained more cells by 3-4 days after inoculation. In contrast, epidermal growth factor enlarges small colonies by flattening the cells, but does not increase appreciably the number of cells per colony until the colony is fairly large. None of the other agents produced the cell spreading effect of epidermal growth factor and all acted as well in the presence of an optimal epidermal growth factor concentration as in its absence. In the case of epidermal cells, the presence of cholera toxin appears to increase the proportion of small cells in growing colonies at all ages. It is believed that it is these smaller size cells which are proliferating in epidermal cell cultures.

The agents described herein can be employed to increase the growth rate of epithelial cells being serially cultivated according to the methods of Green et al. described in detail in U.S. Pat. No. 4,016,036, or in other techniques which may prove to be suitable for epithelial cell growth. In addition, in the treatment of human disease, these same agents should speed up the growth of human epidermis or other epithelia damaged by burns, ulcers, wounds, etc. Thus, these agents can be incorporated into wound dressings, bandages, etc., or can be topically applied in a solution, cream, ointment, spray, salve, or other special vehicles to epithelia where cells are to be stimulated. Such epithelial lesions include those of the skin, cornea, conjunctive mouth, pharynx, vagina, etc.

This invention can be further illustrated by means of the following examples.

EXAMPLE 1

Effect of Cholera Toxin

Cultures were grown in the Dulbecco-Vogt modification of Eagle's medium, supplemented with 20% fetal calf serum and hydrocortisone in an amount of 0.4 µg/ml. Medium was changed twice weekly. Cultures were started by inoculating disaggregated epidermal cells together with $3 \times 10^5$ lethally irradiated 3T3 cells, as described in U.S. Pat. No. 4,016,036. The human epidermal cells were of strain N derived from the foreskin of humans and used between their second and sixth serial transfer.

60 mm tissue culture dishes were inoculated with $10^4$ epidermal cells and $3 \times 10^5$ lethally irradiated 3T3 cells. Cholera toxin was added beginning at the time of inoculation. Epidermal growth factor was added to half of the cultures beginning two days later. Cholera toxin was obtained from Schwartz-Mann, Orangeburg, New York, and epidermal growth factor was prepared from mouse submaxillary glands by the method of Savage and Cohen. C. R. Savage and S. Cohen, "Epidermal Growth Factor and a New Derivative—Rapid Isolation Procedures and Biological and Chemical Characterization," *J. Biol. Chem.*, 247, pp 7609–7611 (1972). Cultures were fixed and stained with Rhodanile blue fourteen days after inoculation.

Cholera toxin stimulated colonial growth strongly and rather uniformly over a range of $10^{-9}$ to $10^{11}$ molar. The effect of $10^{-12}$ molar was clear but of reduced magnitude. A growth-promoting effect could be observed at toxin concentrations as low as $10^{-13}$ molar and no inhibition was observed even at $10^{-8}$ molar. The toxin increased the rate of colony growth in both the presence and absence of an optimal epidermal growth factor (EGF) concentration. The toxin alone did not produce flattening of the colonies; instead, the cells remained closely packed, and the colonies seemed to contain more cells even a few days after inoculation. In the presence of both EGF and the toxin, small colonies showed the effect of EGF in their flattening and pale red staining with Rhodanile blue. As the colonies became larger, they obviously contained more cells than colonies in the presence of EGF alone; they appeared thicker, and stained more intensely red with Rhodanile blue. This was the case at all effective toxin concentrations.

When, from inocula of the same size, cultures were grown in the presence and absence of the toxin, macroscopic colonies frequently seemed up to twice as numerous in the toxin-containing plates. Microscopic examination showed that the difference was probably due to the fact that many colonies aborted in the absence of the toxin and therefore remained below the size at which colonies were usually counted. Abortive colonies have large cells that appear to be termally differentiated.

Once cultures were grown in the presence of cholera toxin at $10^{-9}$ molar, they continued to show the effects of the toxin over a long period even when it was not added to the medium. As $10^{-9}$ molar is four orders of magnitude higher than the minimal effective concentration, it would take some time and many changes of medium to wash out all the toxin. In addition, cholera toxin is known to exert an irreversible action on cellular adenyl cyclase. At least two transfers in the absence of the toxin seemed necessary to restore cellular behavior to that of a control. Thus, cholera toxin exhibits a continuous effect which could be important in in vivo applications.

EXAMPLE 2

Effect of Cholera Toxin on Rate of Cell Multiplication

Following the procedures of Example 1, two experiments were carried out to determine the effect of cholera toxin on the rate of cell multiplication. Cultures were inoculated with $5 \times 10^4$ epidermal cells, strain N, fourth or fifth serial transfer. In both cases, the inoculation was made with $3 \times 10^5$ lethally irradiated 3T3 mouse fibroblast cells. EGF and/or cholera toxin were added. Approximately, exponential growth continued for 8–9 days. 3T3 cells were selectively detached with EDTA and the epidermal cells were trypsinized and counted. The increase in cell number and the average doubling time were calculated from the number of cells harvested and the initial number of colony-forming cells (number of colonies produced). The results are shown below:

| | Average Doubling Time (hrs) From Inoculation to Day 8 or 9 | |
|---|---|---|
| Agent | Experiment 1 Strain N, 4th Transfer | Experiment 2 Strain N, 5th Transfer |
| Control | 29 | 27 |
| Toxin $10^{-9}$ M | 23 | 20 |
| EGF 10 ng/ml | 27 | 24 |
| EGF + Toxin | 22 | 19. |

These data show that the cellular growth rate was markedly accelerated by cholera toxin, both in the presence and absence of EGF.

EXAMPLE 3

Comparative Effect of Dibutyrl Cyclic-AMP and Cholera Toxin on Colony Growth

A frozen stock of Strain N, second transfer, was thawed and $2 \times 10^4$ cells were inoculated with 3T3 cells as described in Example 1. Dibutyryl cyclic-AMP or cholera toxin were added to the two different concentrations, and half the cultures received EGF as well, beginning two days later. Cultures were fixed and stained fourteen days after inoculation.

The results showed that dibutyryl cyclic-AMP also increases colony size, either in the presence or absence of EGF, but its effect is much smaller in magnitude than that of cholera toxin. A concentration of $10^{-4}$ molar produced an increased colony size, and a concentration of $3 \times 10^{-4}$ molar appeared optimal.

Cyclic-AMP and sodium butyrate were also added to the same range of concwntrations, and no effect was seen.

EXAMPLE 4
Effect of Methyl Isobutyl Xanthine

Methyl isobutyl xanthine was tested according to the procedures of Example 1. At a concentration as low as $10^{-6}$ molar, it produced an increase in colony size. At $3 \times 10^{-5}$ molar, it had a stronger effect. The stimulating effect of methyl isobutyl xanthine was evident when EGF was added as well, for the colonies grew most rapidly when both agents were present. The appearance of colonies stimulated by methyl isobutyl xanthine resembled that produced by cholera toxin but the effect of the drug was less marked in all respects. Though it seemed quite obvious microscopically that the colonies stimulated by methyl isobutyl xanthine contained more cells, this was confirmed by cell counts. After selective detachment of 3T3 cells by brief treatment with EDTA, the epidermal cells of sixteen day colonies were disaggregated with trypsin and EDTA and counted. The results are presented below:

| Agent | Epidermal Cells/Dish ($\times 10^{-5}$) |
|---|---|
| None | 1.5 |
| Methyl isobutyl xanthine | 2.2 |
| EGF, 10 ug/ml | 5.0 |
| Methyl isobutyl xanthine + EGF | 15.0. |

It can be seen that though each agent alone increased cell number, the largest effect (10-fold increase) was obtained with a combination of methyl isobutyl xanthine and EGF.

EXAMPLE 5
Effect of Isoproterenol

Isoproterenol was also tested according to the procedures of Example 1. This agent had a stronger effect in increasing colony size than methyl isobutyl xanthine, but a weaker effect than cholera toxin. The most effective concentration was $10^{-5}$–$10^{-6}$ molar. No effect was observed below $10^{-7}$ molar and very few colonies developed at $10^{-4}$ molar.

In contrast to cholera toxin, the effect of isoproterenol was quite quickly reversed after its withdrawal from medium.

EXAMPLE 6
Effect of Cholera Toxin on Other Epithelial Cells

The effect of cholera toxin was tested on cultures of epithelial cells derived from corneal, nasopharyngeal and tracheal epithelium according to the procedures of Example 1. Cultures of adult corneal epithelium cells had been prepared earlier by Sun and Green and stored frozen. See T-T. Sun and H. Green, "Differentiation of the Epidermal Keratinocyte in Cell Culture", Formation of the Cornified Envelope, Cell, 9, pp 511–521 (1976). Human strains of nasopharyngeal and tracheal origin were derived from biopsies.

Cholera toxin was found to have the same growth-promoting activity for these epithelial cells as it displayed for the epidermal cells as described in Example 1. Epithelial cells derived from older donors grew poorly in the absence of toxin, and they soon became impossible to cultivate further, whereas cultivation in the presence of toxin permitted these cells to grow much faster and for a much longer period.

EXAMPLE 7
Effect of Toxin on Epidermal Cells Without Fibroblast Support The effect of cholera toxin on epidermal cell growth in the absence of fibroblast support was compared to growth with fibroblast support employing the growth procedures of Example 1, except as noted.

The supporting irradiated 3T3 cells of a ten-day epidermal culture were selectively removed with EDTA: the epidermal cells were then disaggregated and $1.8 \times 10^5$ cells were transferred into 50 mm dishes either untreated or previously conditioned by prior growth of 3T3 cells. The cultures were fed with medium of different kinds and after ten days were fixed and stained.

At the inoculation density employed, regular medium was totally ineffective in supporting epidermal growth on either untreated or conditioned surfaces. Conditioned medium permitted a few colonies to form, but these aborted while still quite small. When toxin was added to either regular medium or conditioned medium, growth was vastly improved, but remained better in the presence of conditioned medium than in regular medium. Finally, when the toxin was added to medium during its conditioning by 3T3 cells, its subsequent effect on epidermal proliferaton was not as pronounced as when it was added directly to epidermal cultures fed with conditioned medium prepared in the absence of the toxin.

Cholera toxin can, therefore, act directly on epidermal cells. It promoted growth even in the absence of any conditioning by fibroblast products; but this was true only if the cells were present at rather high density, the extent of growth was not comparable to that of fibroblast supported cultures and the cells could not be serially transferred.

EXAMPLE 8
Effects of Cholera Toxin on Cell Size

Epidermal cultures were grown under the procedures of Example 1 in the presence and absence of cholera toxin. All cultures received EGF. At intervals, the 3T3 cells were selectively removed from cultures with EDTA, the epidermal cells were disaggregated and photographed in a hemocytometer chamber. The diameters of the cells were measured as described previously by Sun and Green and histograms were plotted. See T-T. Sun and H. Green, "Differentiation of the Epidermal Keratinocyte at Cell Culture: Formation of the Cornified Envelope." Cell, 9, pp 511–521 (1976).

All cell populations showed the expected skewed distribution of cell sizes. The presence of the toxin increased the proportion of small cells in growing colonies of all ages examined. For colonies growing in the presence of toxin, the proportion of cells having a diameter between 9.5 and 14 $\mu$m was nearly double that of the corresponding control. If the cells with mean diameter of up to 16.5 $\mu$m were also included in the category of small cells, a difference between toxin-grown and control cells was preserved, though it was of somewhat smaller magnitude. It is clear then that the toxin increased the abundance of the small size category to which the proliferating cells are known to belong.

Those skilled in the art will recognize that there are many equivalents to the specific embodiments described herein. For example, although the agents employed to promote growth of epithelial cells have been chemical agents which increase cellular cyclic-AMP, other techniques for increasing the levels of cellular cyclic-AMP, such as the use of physical means might also be employed to both increase the level of cyclic-AMP and to stimulate growth of epithelical cells. Such equivalents are intended to be encompassed within the following claims.

What is claimed is:

1. A method of promoting growth of human epithelial cells in culture comprising contacting said cells with an effective growth-promoting amount of an agent capable of increasing cellular cyclic-AMP and cell multiplication.

2. The method of claim 1 wherein the agent capable of increasing cellular cyclic-AMP comprises cholera toxin.

3. In a method for serially culturing epithelial cells, including the steps of forming a culture of epithelial cells in a culture medium containing fibroblast cells treated to prevent their multiplication and at a density sufficient to allow epithelial colonies to grow, maintaining said culture under conditions conducive to cell growth whereby epithelial colonies are formed, harvesting said epithelial colonies, and serially replating said epithelial cells into subcultures:
the improvement comprising supplying an effective growth-promoting amount of an agent capable of increasing cellular cyclic-AMP to said culture in order to stimulate cell multiplication.

4. A method of claims 1 or 2 wherein said epithelial cells comprise stratified squamous epithelium.

5. A method of promoting multiplication of human epithelial cells in culture by increasing the level of cyclic-AMP in said cells.

6. A method of claims 1 or 5 wherein said epithelial cells are grown in the presence of fibroblast cells treated to prevent their multiplication or medium conditioned by fibroblast cells.

7. In a method for serially culturing epithelical cells, including the steps of forming a culture of epithelial cells in a culture medium containing fibroblast cells treated to prevent their multiplication and at a density sufficient to allow epithelial colonies to grow, maintaining said culture under conditions conducive to cell growth whereby epithelial colonies are formed, harvesting said epithelial colonies, and serially replating said epithelial cells into subcultures:
the improvement comprising supplying an effective growth-promoting amount of an agent capable of increasing cellular cyclic-AMP to said culture.

8. The improvement of claim 7 wherein said agent is selected from the group consisting of cholera toxin, methyl isobutyl xanthine and isoproterenol.

9. A method of claim 8 wherein said epithelial cells comprise stratified squamous epithelium.

10. A method of claim 9 wherein said culture contains fibroblast cells treated to prevent their multiplication, said treated cells being present at a density sufficient to allow epithelial colonies to grow.

11. A method of claim 10 wherein said culture additionally contains an effective growth-promoting amount of epidermal growth factor.

12. The method of claim 7 wherein the agent capable of increasing cellular cyclic-AMP comprises cholera toxin.

13. A method for serially culturing epithelial cells, comprising the steps of:
forming a culture of epithelial cells in a culture medium containing fibroblast cells treated to prevent their multiplication and at a density sufficient to allow epithelial colonies to grow and/or medium sufficiently conditioned by fibroblast cells to allow epithelial colonies to grow;
supplying an effective growth-promoting amount of cholera toxin capable of increasing cellular cyclic-AMP to said culture;
maintaining said culture under conditions conducive to cell growth whereby epithelial colonies are formed;
harvesting said epithelial colonies; and,
serially re-plating said epithelial cells into subcultures.

* * * * *